United States Patent [19]

Kossovsky et al.

[11] Patent Number: 5,462,751

[45] Date of Patent: * Oct. 31, 1995

[54] BIOLOGICAL AND PHARMACEUTICAL AGENTS HAVING A NANOMERIC BIODEGRADABLE CORE

[75] Inventors: Nir Kossovsky; H. James Hnatyszyn; Andrew Gelman, all of Los Angeles, Calif.

[73] Assignee: The Regeants of the University of California, Oakland, Calif.

[ * ] Notice: The portion of the term of this patent subsequent to Jan. 12, 2010, has been disclaimed.

[21] Appl. No.: 146,536

[22] Filed: Nov. 1, 1993

Related U.S. Application Data

[63] Continuation-in-part of Ser. No. 199, Jan. 4, 1993, Pat. No. 5,334,394, which is a continuation-in-part of Ser. No. 690,601, Apr. 24, 1991, Pat. No. 5,178,882, which is a continuation-in-part of Ser. No. 542,255, Jun. 22, 1990, Pat. No. 5,219,577.

[51] Int. Cl.[6] ................................................ A61K 9/14

[52] U.S. Cl. .................. 424/494; 424/93.6; 424/490; 424/493; 424/498; 514/2; 514/6; 514/951; 514/970

[58] Field of Search ................... 424/490, 493, 424/494, 498

[56] References Cited

U.S. PATENT DOCUMENTS

| | | | |
|---|---|---|---|
| 4,501,726 | 2/1985 | Schröder et al. | 424/1.1 |
| 4,904,479 | 2/1990 | Illum | 424/490 |
| 5,178,882 | 1/1993 | Kossovsky et al. | 424/494 |
| 5,219,577 | 6/1993 | Kossovsky et al. | 424/494 |

*Primary Examiner*—Thurman K. Page
*Assistant Examiner*—James M. Spear
*Attorney, Agent, or Firm*—Poms, Smith, Lande & Rose

[57] ABSTRACT

A biologically active composition made up of biodegradable core particles which are coated with a layer that is designed to allow attachment of biologically active agents without denaturing them. The composition may further include an exterior targeting membrane which provides selective targeting to specific receptors.

8 Claims, No Drawings

BIOLOGICAL AND PHARMACEUTICAL AGENTS HAVING A NANOMERIC BIODEGRADABLE CORE

BACKGROUND OF THE INVENTION

This is a continuation-in-part of application Ser. No. 08/000,199 now U.S. Pat. No. 5,334,394 which was filed on Jan. 4, 1993 which is a continuation-in-part of Ser. No. 07/690,601, now U.S. Pat. No. 5,178,882 which was filed on Apr. 24, 1991 which is a continuation-in-part of application Ser. No. 07/542,255, now U.S. Pat. No. 5,219,577 which was filed on Jun. 22, 1990.

FIELD OF THE INVENTION

The present invention relates generally to synthetic biologically active compositions which have a microparticulate core. More particularly, the present invention relates to biologically active compositions where the microparticulate core is biodegradable.

DESCRIPTION OF RELATED ART

The attachment of biologically active proteins, peptides or pharmacologic agents to various carrier particles has been an area of intense investigation. These conjugated biological systems offer the promise of reduced toxicity, increased efficacy and lowered cost of biologically active agents. As a result, many different carrier models are presently available. (Varga, J. M., Asato, N., in Goldberg, E. P. (ed.): *Polymers in Biology and Medicine*. New York, Wiley, 2, 73–88 (1983). Ranney, D. F., Huffaker, H. H., in Juliano, R. L. (ed.): *Biological Approaches to the Delivery of Drugs*, Ann. N.Y. Acad. Sci., 507, 104–119 (1987).) Nanocrystalline and micron sized inorganic substrates are the most common carriers and proteins are the most commonly conjugated agents. For example, gold/protein (principally immunoglobulin) conjugates measuring as small as 5 nm have been used in immunological labeling applications in light, transmission electron and scanning electron microscopy as well as immunoblotting. (Faulk, W., Taylor, G., *Immunochemistry* 8, 1081–1083 (1971). Hainfeld, J. F., *Nature* 333, 281–282 (1988).)

Silanized iron oxide protein conjugates (again principally antibodies) generally measuring between 500 and 1500 nm have proven useful in various in vitro applications where paramagnetic properties can be used advantageously. (Research Products Catalog, Advanced Magnetics, Inc., Cambridge, Mass., 1988–1989.) Ugelstad and others have produced gamma iron oxides cores coated with a thin polystyrene shell. (Nustad, K., Johansen, L., Schmid, R., Ugelstad, J., Ellengsen, T., Berge, A.: Covalent coupling of proteins to monodisperse particles. Preparation of solid phase second antibody. Agents Actions 1982; 9:207–212 (id. no. 60).) The resulting 4500 nm beads demonstrated both the adsorption capabilities of polystyrene latex beads as well as the relatively novel benefit of paramagnetism.

Carrier systems designed for in vivo applications have been fabricated from both inorganic and organic cores. For example, Davis and Illum developed a 60 nm system comprised of polystyrene cores with the block copolymer poloxamer, polyoxyethylene and polyoxypropylene, outer coats that showed a remarkable ability to bypass rat liver and splenic macrophages. (Davis, S. S., Illum, L., *Biomaterials* 9, 111–115 (1988)). Drug delivery with these particles has not yet been demonstrated. Ranney and Huffaker described an iron-oxide/albumin/drug system that yielded 350–1600 nm paramagnetic drug carriers. (Ranney, D. F., Huffaker, H. H., In, Juliano, R. L. (ed.): *Biological approaches to the delivery of drugs*, Ann. N.Y. Acad. Sci. 507,104–119 (1987).) Poznasky has developed an enzyme-albumin conjugate system that appears to decrease the sensitivity of the product to biodegradation while masking the apparent antigenicity of the native enzyme. (Poznasky, M. J.: Targeting enzyme albumin conjugates. Examining the magic bullet. In, Juliano, R. L. (ed.): *Biological approaches to the delivery of drugs*, Annals New York Academy Sciences 1987; 507-211:219.)

Shaw and others have prepared and characterized lipoprotein/drug complexes. (Shaw, J. M., Shaw, K. V., Yanovich, S., Iwanik, M., Futch, W. S., Rosowsky, A., Schook, L. B.: Delivery of lipophilic drugs using lipoproteins. In, Juliano, R. L.(ed.): *Biological approaches to the delivery of drugs*, Annals New York Academy Sciences 1987; 507:252–271.) Lipophilic drugs are relatively stable in these carriers and cell interactions do occur although little detail is known.

In any conjugated biological composition, it is important that the conformational integrity and biological activity of the adsorbed proteins or other biological agents be preserved without evoking an untoward immunological response. Spacial orientation and structural configuration are known to play a role in determining the biological activity of many peptides, proteins and pharmacological agents. Changes in the structural configuration of these compounds may result in partial or total loss of biological activity. Changes in configuration may be caused by changing the environment surrounding the biologically active compound or agent. For example, pharmacologic agents which exhibit in vitro activity may not exhibit in vivo activity owing to the loss of the molecular configuration formerly determined in part by the in vitro environment. Further, the size and associated ability of the carrier particle to minimize phagocytic trapping is a primary concern when the composition is to be used in vivo. All of these factors must be taken into account when preparing a carrier particle.

Biochemical phenomena consist of binary interactions between pairs of molecules. Common names for such biochemically reactive pairs ("BRP's") include but are not limited to immunological pairs, ligand-receptor pairs, enzyme-substrate pairs, drug-receptor pairs, catalyst-reactant pairs, catalyst-substrate pairs, absorbate-absorbent pairs, adsorbate-adsorbent pairs, and toxin-ligant pairs. On a molecular level, nearly all biochemical phenomena between such pairs involve the spatial recognition of one molecule by another, and such recognition serves as the means by which energy and information are transmitted, products are generated, responses are initiated and complex biological structures are built.

The process of spatial recognition implies of both regioselective and stereoselective interactions among BRP's. One member of a BRP, constrained by fundamental biophysical laws, may interact with the other member of a BRP if and only if both members are physically conformed within some bounded set of possible spatial arrangements and if both members have their respective interactive regions unencumbered. The environment within which BRP's interact affect greatly the process of spatial recognition. Environments that contain spatial mobility or encumber molecular regions may, depending on the degree of constraint and the resulting spatial conformation, either promote or inhibit BRP interactions.

An example of the former is surface activation of synthetic chemical reactions in a process known as "solid phase synthesis." Solid phases, either as solid glassy polymers, crystalline materials, or complex macromolecular polymers have been features of synthetic biochemistry since the early 1960's. Their use was advanced largely by Merrifield for facilitating peptide synthesis and for which he received the Nobel Prize for Chemistry in 1984. They became widely popular because the solid-phase method offered simplicity, speed, avoidance of intermediate isolation, and automation. The principal limitation in the widespread use of solid phases has been the empirical observation that only a few surfaces have been effective BRP interaction promoters. Drug delivery systems which are used for in vivo delivery of biologically active agents, tend to be very complex. Most have some advantages that give them promise and possibility for further development. Most are also riddled with problems ranging from low drug load to in vivo instability. Drug delivery systems which are able to deliver a moderate dose of therapeutic agent to a specific target cell are highly desirable. This type of delivery system should provide a binding of the carrier to the cell via a receptor and a mechanism of internalization where the drug is liberated to the intracellular space from the carrier. The carrier should also be biodegradable and not induce any type of immune reaction or response. The delivery system should be specific, with high efficacy and low non-targeted toxicity. It should be convenient to administer, manufacture, and be economically viable for both the patient and the manufacturer.

Although numerous different carrier particles and systems have been developed, there is a continuing need to provide carrier particles and systems for both in vivo and in vitro application which meet most, if not all, of the above stated objectives.

SUMMARY OF THE INVENTION

In accordance with the present invention, biologically active peptides, proteins or pharmacological agents are attached to a biodegradable core particle to provide a wide variety of biologically active compositions. The invention is based in part on the discovery that the surface of ultrafine particles (nanocrystalline particles) can be modified with a surface coating to allow attachment of biologically active moieties to produce compositions wherein the naturally occurring structural environment of the moiety is mimicked sufficiently so that biological activity is preserved. The core particle, with the surface coating and attached moiety, is further coated with a targeting agent, such as a biologically active ligand or phospholipid membrane complex.

The invention is also based in part on the discovery that biodegradable core particles may be assembled with biologically active or pharmaceutical agents to form a biologically active core which is further treated with a targeting ligand or membrane complex to provide selective targeting of the biochemically active core in vivo.

As a feature of the present invention, the nanocrystalline core is composed of brushite which is composed of crystalline calcium phosphate (brushite). This material is biodegradable, inexpensive and is found in human beings as a substrate of bone synthesis. The brushite particles may be synthesized at a nanomeric size (between approximately 5 nm and 150 nm). This small size allows the drug delivery construct to be small enough to avoid uptake by the Reticulo-Endothelial System (RES) of the body and deliver the drug or biologically active agent in vivo without non-specific toxicity or loss of drug to macrophages.

The brushite core may be co-crystallized with a drug or agent for sustained release and protection of the drug from the physiological environment. Conversely, the brushite core may be coated, as described above with a sugar, such as cellobiose or pyridoxal-phosphate to improve its surface attachment characteristics. The sugar coat allows for the binding of drugs and other biological agents in their active or inactive forms, without alteration. The sugar helps to maintain the conformation of the drug or agent that is adsorbed to its surface. This core construct is capable of carrying a moderate drug or agent load, depending upon the size of the biological agent.

As a feature of the present invention, the brushite based particle is targeted to a specific tissue or cell type. In order to achieve this targeting, the construct has a targeting ligand or a primed phospholipid membrane tightly adsorbed to its surface. The membrane may contain proteins, receptors and carbohydrates which provide targeting of the vehicle. The membrane also serves to further maintain the stability of the biological agent and the integrity of the construct. This membrane may be derived from cell membranes, viral envelopes (see U.S. Pat. No. 5,178,882), or other specifically engineered or synthesized membranes. Due to the very small size of the biodegradable core particle delivery system, multiple layers of membranes may be adsorbed to the core particle to increase the efficiency of targeting.

As one aspect of the present invention, biodegradable nanocrystalline particles are used to prepare a decoy virus wherein the DNA or RNA core of the virus is replaced by the microparticle. The microparticle is chosen to be approximately the same size as the viral core so that the conformation of the surrounding protein coat accurately mimics the native virus. The resulting viral decoy is incapable of infectious behavior while at the same time being fully capable of effecting an immune response and otherwise being antigenically bioreactive.

The biologically active microparticles in accordance with the present invention have wide-ranging use depending upon the type of biologically active compound which is attached to the biodegradable microparticle core. When viral protein from HIV is attached to the microparticle core, the result is a decoy virus which may be used as an AIDS vaccine, diagnostic tool or antigenic reagent for raising antibodies. Non-viral protein or antigen coatings may be selected and structured for use in raising specific antibodies or as a diagnostic tool. Further, the microparticles can function as a pharmacological agent when compounds having pharmacological activity are attached to the biodegradable core particle.

In accordance with the present invention, biodegradable core particles having diameters of less than about 1000 nanometers are used to anchor enzymes or other catalytic particles without denaturing the catalyst. Surface coating of the core particles provides an anchoring surface which prevents substantial alteration of the catalysts which might otherwise occur when the catalysts are attached directly to the particle surface. The coated particles are also useful for anchoring catalyst-substrate (enzyme-substrate) pairs or other bioreactive pairs (BRP's) without destroying the catalytic activity of the BRP's.

The above-discussed and many other features and attendant advantages of the present invention will become better understood by reference to the following detailed description.

DETAILED DESCRIPTION OF THE INVENTION

The present invention has wide application to immunologic procedures and methods wherein antigenic material, biologically reactive pairs (BRP's) or other biologically active moieties are utilized. These areas of application include vaccination agents, antigen agents used to raise antibodies for subsequent diagnostic uses and antigenic compounds used as diagnostic tools. The composition of the invention can also be used in a wide variety of other applications where there is a need to target pharmaceuticals or other biologically active agents to particular cell types in both in vivo and in vitro environments.

The compositions of the present invention include biodegradable nanocrystalline core particles (diameters of less than 1000 nm) which are coated with a surface energy modifying layer that promotes bonding of proteins, peptides or pharmaceutical agents to the particles. The coating modifies the surface energy of the nanocrystalline core particles so that a wide variety of immunogenic proteins, peptides and pharmaceutical agents may be attached to the core particle without significant loss of antigenic activity or denaturation. The result is a biologically active composition which includes a biologically inert core. The end use for the compositions of the present invention will depend upon the particular protein, peptide or pharmacological agent (including gene therapy) which is attached to the coated core particle. For example, proteins or peptides having antigenic activity may be attached to provide compositions useful as immunodiagnostic tools. Viral fragments or protein coatings having immunogenic activity may be attached to provide a vaccine. Also, pharmacological agents may be attached to provide compositions which are useful in treating diseases. Also, gene segments or antisense fragments may be attached which are useful in treating diseases.

Examples of individual catalysts which may be attached to the coated core particles include tissue plasminogen activator (whole and partial domains), trypsin inhibitor, cytrochromes, Ferredoxin, phosphotransferase, acyltransferase, papain, Lys C, Arg C, Trypsin, Coagulation factor V, XIIa, XIa, VIIa, Complement factor C3, C3b and properdin.

Bioreactive pairs (BRP's), such as enzyme-substrate pairs, may also be attached to the coated core particles. Exemplary enzyme-substrate pairs include: lysozyme-chitin pairs, where the lysozyme catalyzes the hydrolysis of NAM and NAG glycosidic bonds; ribonuclease-RNA pairs where the ribonuclease catalyzes the hydrolysis of RNA; carboxypeptidase A—carboxyl terminal polypeptide pairs where the enzyme catalyzes the hydrolysis of the carboxyl-terminal peptide bond in the polypeptide chain; serine, zinc, thiol and carboxyl proteases-protein pairs where the protease catalyze the degradation of the protein; NADH-Q reductase—NADH pairs where the reductase catalyzes the oxidation of NADH and the reduction of Q; glutathione seductase-glutathione pairs; acetylcholinesterase-acetylcholine pairs; Lys C; Arg C; acyl and acyltransferase; aspartate and aspartate carbomyltransferase; elastase; and the cytochromes.

Other biochemically reactive pairs (BRP) which can be immobilized on to the coated solid surfaces in accordance with the present invention include members of immunological pairs, ligand-receptor pairs, drug-receptor pairs, catalyst reactant pairs, catalyst-substrate pairs, absorbate-absorbent pairs, adsorbate-adsorbent pairs, and toxin-ligand pairs. Such members include but are not limited to:

immunological pair members such as IgG, IgM, IgA, IgE and IgD, whole or in part as in Fc or Fab fractions, polyclonal or monoclonal, with recognition sites for epitopes on cells (cell surface antigens) such as CD1, CD3, CD4, CD8, CD11, CD25, CD68; viral epitopes such as EBVgp350, HIVp24, HIVgp120, MS virus coat protein (bacteriophage) other viral antigens, bacterial antigens, fungal antigens, and known viruses, fungi, bacteria, prions and protozoa.

ligand-receptor pair members such as lectins and lectin binding sites such as FVIII receptor; HDL and HDL receptor cellular receptor site; hormones such as estrogen and estrogen receptor sites; antibiotics; ribosomal proteins; FK506 and FK506 binding protein; ricin and cell target; phosphotyrosine recognition domain SH2 (RSV) and phosphotyrosine; and (oligo)nucleopeptides and their corresponding antisense nucleopeptide.

drug-receptor pair members such as epinephrine and adrenergic receptors, methadone and opiate receptors, DNA chelating agents such as adriamycin, etc.

catalyst-reactant pair members such as iron and superoxide, rhodopsin kinase and rhodopsin, hydrogen peroxide and luminol, horseradish peroxidase and hydrogen peroxide.

adsorbent-adsorbate pair members, such as trypsin-trypsin inhibitor, biotin-biotin repressor (*E. coli*) and subtilisin and subtilisin inhibitor.

toxin-ligand pair members such as strychnine and the glycine receptor, hemoglobin and carbon monoxide, and organophosphate compounds (sarin, tabun, parathion, dimefox, malathion, diazinon) and acetylcholinesterase; muscarinic receptor and neurotoxins (Neurotoxin I from *S. helianthus*' scorpion neurotoxin); verotoxin and colonic mucosal epithelial receptor; enterotoxin and colonic mucosal epithelial receptor.

One or both of the members of the BRP may be initially bound to the modified surface. In general, the enzyme or catalyst will be bound first and substrate or reactant bound later during actual interaction between the enzyme and substrate or catalyst and reactant.

For preparing decoy viruses for use as vaccines, particles having diameters of between about 10 to 200 nanometers are preferred since particles within this size range more closely mimic the diameter of DNA and RNA cores typically found in viruses.

The core particles may be made from a variety of biodegradable materials including polymers or ceramics. Preferred ceramic materials include brushite composed of calcium phosphate dihydrate, and tricalcium phosphate and iron oxide. Preferred biodegradable polymers include polylactide, polygalactide and polylysine. Particles made from brushite are particularly preferred.

Particles made from the above materials having diameters less than 1000 nanometers are available commercially or they may be produced from progressive nucleation in solution (colloid reaction), or various physical and chemical vapor deposition processes, such as sputter deposition (Hayashi, C., *J. Vac. Sci. Technol.* A5 (4), July/August 1987, pgs. 1375–1384; Hayashi, C., *Physics Today*, December 1987, pgs. 44–60; MRS Bulletin, January 1990, pgs. 16–47).

The biodegradable core particles may be coated with a substance that provides a threshold surface energy to the particle or other surface which is sufficient to cause binding to occur without that binding being so tight as to denature biologically relevant sites. Coating is preferably accomplished by suspending the particles in a solution containing the dispersed surface modifying agent. It is necessary that the coating make the surface of the particle more amenable to protein, nucleotide or peptide attachment.

Suitable coating substances in accordance with the present invention include carbohydrates, carbohydrate derivatives, and other macromolecules with carbohydrate-like components characterized by the abundance of —OH (hydroxyl) side groups. The coatings may include but are not limited to:

- short chain carbohydrates including glucose, sucrose, cellobiose, nystose, triose, dextrose, trehalose, glucose, lactose, maltose, etc.
- hydroxyl rich weak acids such as citrate, fumarate, succinate, isocitrate, oxaloacetate, malate, etc.
- nucleotide-like molecules with pendant carbohydrate or phosphate groups such as pyridoxyl-5-pyrophosphate, thiamine pyrophosphate, uridine-diphosphate-glucose, glucose-1-phosphate, adenosine, nicotinamide-adenine-diphosphate, etc.
- derivatives of carbohydrates such as nitrocellulose
- complex polymeric carbohydrates and derivatives such as dextran, glycogen, etc.

Preferred coating materials include pyridoxyl-5-pyrophosphate, citrate and cellobiose.

In a preferred process for coating, the biodegradable particles are suspended in a coating solution. The coating solution into which the core particles are suspended contains, for example, from 1 to 30 weight/volume percent of the coating material. The solute is preferably double distilled water (ddH$_2$O). The amount of core particles suspended within the coating solution will vary depending upon the type of particle and its size. Typically, suspensions containing from 0.1 to 10 weight/volume percent are suitable. Suspensions of approximately 1 weight/volume percent of particles are preferred.

The core particles are maintained in dispersion in the coating solution for a sufficient time to provide uniform coating of the particles. Sonication is the preferred method for maintaining the dispersion. Dispersion times ranging from 30 minutes to a few hours at room temperature are usually sufficient to provide a suitable coating to the particles. The thickness of the coating is preferably less than 5 nanometers. Thicknesses of the coating may vary provided that the final core particles include a uniform coating over substantially all of the particle surface.

The particles are separated from the suspension after coating and may be stored for future use or redispersed in a solution containing the protein or peptide to be attached to the particles. Alternatively, the coated particles may be left in the suspension for further treatment involving attachment of the desired protein or peptide.

The term "biodegradable" as used herein means any core particle which decomposes or otherwise disintegrates after prolonged exposure to a mammalian in vivo environment. To be biodegradable, the core particle should be substantially disintegrated within a few weeks after introduction into the body.

The protein or peptide which is applied to the coated particles may be selected from a wide variety of proteins or peptides. Those having antigenic properties are preferred when a vaccine is required. The protein can be the viral protein coat from a selected virus or immunogenic portion thereof. The viral protein coat is isolated according to known separation procedures for isolating and separating viral proteins. The viral coating is the preferred protein because the viral coating is where the antigenic activity of viruses is known to be located. Typically, the virus is digested or solubilized to form a mixture of viral proteins. The viral proteins are then separated by liquid chromatography or other conventional process into the various protein particle fractions and dialyzed to remove impurities.

Suitable viruses from which viral protein particles can be separated and isolated include Epstein-Barr virus, human immunodeficiency virus (HIV), human papilloma virus, herpes simplex virus and pox-virus. Preparations of a wide variety of antigenic protein materials may also be purchased commercially from supply houses such as Microgene Systems, Inc. (400 Frontage Road, West Haven, Conn. 06516), Amgen Corporation (1900 Oak Terrace Lane, Thousand Oaks, Calif. 91320-1789) and Cetus Corporation (1400 53rd Street, Emeryville, Calif. 94608 and Advanced Biotechnology, Inc. (Columbia, Md.). Synthetic peptides and/or proteins which correspond to naturally occurring viral particles may also be utilized.

With respect to HIV, any of the viral fragments which are known to elicit an immune response can be used. Suitable viral fragments include gp120, gp160, gp41, and core proteins (p24). Any of the known techniques for preparing HIV fragments may be used including recombinant methods.

Other biologically active proteins and peptides that can be attached include enzymes, hormones, transport proteins and protective proteins. Human serum transferrin, plasminogen activator and coagulation factors, in addition to the pharmacologic agents amphotericin, taxol and insulin, are examples.

The procedure for attaching the antigens or other protein to the coating on the core particles involves suspending the coated core particles in an aqueous solution containing the antigen. The presence in the solution of materials that may preferentially attach to the particle surface is often not advantageous. For example, the dispersion agents present in the solution may create an undesirable coating on the suspended particles prior to protein attachment. Water miscible solvents such as methanol or ethanol may be used. The aqueous solution of coated microparticles can be agitated sufficiently to provide a uniform suspension of the particles. Typically, the amount of particles in solution will be between about 0.5 mg per milliliter of solution and 5 mg per milliliter of solution. Sonication is a preferred method for providing a uniform suspension of the coated particles in solution.

The suspension of coated particles and antigens must be within certain parameters for protein attachment and self assembly to occur. The temperature of the particle solution should be between 1° C. to 45° C. Certain proteins and pharmaceutical agents may be bound to the coated particles in distilled water. Salts may be added to the solution for reactions between coated particles and proteins and other pharmaceutical agents which are unstable or will not disperse readily in distilled water. In general, the salt solutions should be formulated so that the ionic balance (in mM) does not exceed: K=300–500; Na=30–70; Cl=40–150; Ca=0.0003–0.001; and Mg=0.0003–0.001. The oxygen tension of the solution is, advantageously, less than 10% in a solution sparged initially by helium and then gassed with helium, nitrogen and carbon dioxide. The pH of the solution is, advantageously, slightly acidic (relative to blood), with a value, preferably, of between 6.8 to 7.2. An exemplary solution for dispersion of the coated microparticles and for protein attachment is an aqueous solution containing: 0.0360 milligrams MgSo$_4$ per liter, 0.0609 milligrams MgCl$_{2.6}$H$_2$O, 0.0441 milligram CaCl$_{2.2}$H$_2$O, 22.823 grams K$_2$HPO$_4$, 13.609 grams KH$_2$PO$_4$, 7.455 grams KCl, and 4.101 gram sodium acetate. The pH of this solution is adjusted to 6.8.

The coated particle cores with the attached protein can be separated from the ionic growth medium and stored for further use. The coated particles may be stored by any of the conventional methods typically used for storing antigenic compounds or antibodies. For example, the coated particles may be freeze dried (lyophilized) or stored as a suspension in a compatible solution. When used as a vaccine, the particles coated with a vital protein coat are injected or otherwise administered to the individual according to conventional procedures. Any pharmaceutically acceptable carrier solution or other compound may be used in administering the coated particles to the individual. When used for diagnostic purposes in vitro, the protein coated particles are suspended in solution and used in the same manner as other antigenic compounds. The same is true for use of the protein coated particles for raising antibodies. The same protocol and procedures well known for using antigens to produce antibodies may be used wherein the protein coated particles of the present invention are substituted for normally used antigenic compounds.

When targeting of the coated particle and attached biologically active agent is desired, the particles may be coated with a target ligand or a phospholipid membrane complex which is reactive with receptors on particular cells. Exemplary target ligands include HIV coat proteins (gp160, 41, 120) corona virus coat proteins, EBV coat proteins (gp350). Any membrane bound ligand/receptor may be used. These ligands are attached to the particle complex in the same manner as attachment of the biologically active agents discussed above.

The lipids used to coat the biodegradable nanocrystalline particle and bound agent may also be the same lipids commonly used to form liposomes. Suitable lipids include phospholipids such as phosphatidylcholine, cholesterol and phosphatidylserine. The lipids may also be derived directly from natural sources. Such lipids include viral membranes and other lipid bound biochemically reactive pairs. The lipid layer is applied to the nanocrystalline core particle and bound to a biologically active agent in the same manner as the surrogate red blood cells described in copending application Ser. No. 08/029,896.

The core particle and bound agent do not need to be totally covered with a lipid layer. Preferably, the amount of lipid used to coat the particle will be sufficient to coat the entire particle.

In certain situations, it is desirable to attach the biochemically active agent directly to the biodegradable core particles. This direct attachment is preferably accomplished by co-crystallizing the biodegradable core particle with the biochemically active agent. For example insulin, taxol or (DNA, RNA) gene fragments may be co-crystallized with brushite to form drug loaded particles which provide sustained release of the drug while providing protection of the drug in vivo. This direct attachment reduces biological activity.

The following non-limiting examples describe certain aspects of the present invention in greater detail.

EXAMPLE 1

Preparation of Brushite Nanocrystalline Particles Coated With P5P

1. Using two 60 cc syringes and a T-Luer lock, inject 50 mls of 0.75 m $CaCl_2$ and 50 mls of 0.25 m $Na_2HPO_4$ into a 120 ml pharmaceutical bottle in the cup sonicator. Sonicate for 30 minutes at room temperature to form suspension of brushite particles.

2. Spin the brushite preparation down in the centrifuge using the bucket rotor at 3000 rpm for 15 minutes to remove unreacted components.

3. Resuspend the brushite particles in 50 mls of HPLC grade water and mix well. Spin down at 3000 rpm for 15 minutes. Repeat step 3, three times (3×).

4. Add 1.0 ml of 100 mg/ml pyridoxal-5-phosphate (P5P) and incubate for 30 minutes on a rocker arm at room temperature.

5. Lyophilize overnight.

6. Resuspend the P5P-brushite preparation in 50 mls of 0.1 n sodium hydroxide. Mix well. Spin down at 3000 rpm for 20 minutes. This removes the excess P5P. (This step may not have to be completed with all carbohydrates. Centrifugation and subsequent washing steps may be adequate.)

7. Resuspend in 50 mls of PBS and spin down at 3000 rpm for 15 minutes. Repeat step 8 three times (3×). This removes the sodium hydroxide.

8. Resuspend pellet in 50 mls of HPLC grade water and spin down at 3000 rpm for 15 minutes. Repeat step 9 three times (3×). This removes the PBS.

9. Resuspend the pellet in 4.0 mls of HPLC water and 1.0 ml of 100 mM of sodium citrate to pH 7.2.

10. Sonicate for 15 minutes at room temperature to form suspension of particles which is ready for attachment of biochemically active agent.

EXAMPLE 2

Preparation of Brushite Nanocrystalline Particles Coated with Cellobiose

The same procedure as described in Example 1 is followed except that cellobiose is substituted for P5P. The cellobiose coating is applied to the particles by suspending the particles in a stock solution of cellobiose. The cellobiose stock solution is a 292 mM solution made by dissolving 1.000 gram of cellobiose in 9.00 mls of $ddH_2O$. Solution is accomplished at approximately 70° C. in order to promote quick dissolution. The resulting cellobiose solution is filter sterilized through a rinsed 0.45 micron filter with the final volume being adjusted to 10.00 ml.

Sufficient cellobiose stock solution is added to 150 microliters of the ultrafine biodegradable particle dispersion so that the final concentration of the particle is 1.00 percent (w/v) or 29.2 mM. A typical volume for preparation is 2.0 mls which is mixed four or five times by the action of a micro-pipetor. After mixing, the dispersion is allowed to equilibrate for two hours. Demonstration of successful coating of the particles is provided by measuring the mobility of the particles (coated and uncoated) on a Coulter DELSA 440 doppler energy light scatter analyzer. The coated particles exhibit a relatively low mobility compared to the non-coated particles. Measurements are also taken at various dilute salt concentrations to ensure that the observations with respect to mobility are not artifactual.

The coated particles are then used to attach antigenic proteins, peptides or pharmacological agents to prepare bioreactive particles.

EXAMPLE 3

Preparation and Surface Adsorption of Human Serum Transferrin Protein of Brushite Particles Coated With Cellobiose Brushite nanocrystalline particles are prepared as set forth in Example 2.

To adsorb protein to the cellobiose coated nanocrystalline cores, the core sample is diluted to 10.0 ml with $Ca^{++}$ and $Mg^{++}$ free phosphate buffered saline (Gibco). Forty (40.0) µg of purified human serum transferrin (4 µg/µl) (Gibco), whose antigenicity is verified by ELISA, is then added to a 10 ml stir cell (Spectra). The sample is then left to stir slowly for 30 minutes, taking great care not to allow foaming. After the addition period, 15 ml of $Ca^{++}$ and $Mg^{++}$ free phosphate buffered saline (Gibco) is then washed through the cell under a 2 psi nitrogen gas pressure head. After washing, the sample is again concentrated to 1.00 ml under $N_2$ and a 500 µl sample is removed for analysis by photon correlation spectroscopy, Doppler electrophoretic light scatter and transmission electron microscopy as detailed below.

Conformational integrity is assessed by measuring the retained antigenicity of the bound protein. To the sample cell, 50.0 µl of rabbit polyclonal anti-human transferrin antibody (Dako), whose antigenicity is confirmed by ELISA, is added to the concentrated 1.0 ml reaction product at 37.5° C. with gentle stirring. After a 30 minute incubation period, 15 ml of $Ca^{++}$ and $Mg^{++}$ free phosphate buffered saline (Gibco) is then washed through the cell under a 2 psi nitrogen gas pressure head and the reaction volume is again reduced to 1.0 ml.

A 200 µl aliquot of blocking agent, 1% w/v bovine serum albumin in divalent free saline, is added followed by a 10 minute equilibration period. The secondary antibody, 30 nm gold conjugated goat anti-rabbit polyclonal IgG (Zymed), is then added and the reaction mixture is allowed to incubate for 30 minutes. A sample is removed, chopped on a transmission electron microscopy grid, and vacuum dried. The mixture is again washed with 15 ml of divalent free saline under a nitrogen pressure head and then fixed with glutaraldehyde. One ml of 3% solid bovine collagen (Collagen Corp.) is then added to the mixtures and the composite is ultracentrifuged at $10^6 \times g$ for 30 minutes yielding a pellet that is then routinely processed as a biological specimen for transmission electron microscopy.

Following transferring binding, the Brushite/cellobiose/protein conjugates will measure about 150 nm. The biological activity of protein absorbed to the surface of carbohydrate-treated nanocrystalline TCP particles is preserved.

EXAMPLE 4

Preparation and Characterization of Epstein-Barr Virus Decoys

Nanocrystalline brushite particles were synthesized as previously described in Example 1.

Elutriated sucrose gradient purified Epstein-Barr virus (EBV) acquired from the B95-8 cell line are purchased from Advanced Biotechnologies, Inc., Columbia Md. Each viral aliquot contains approximately $5.00\times10^{10}$ virus particles/ml suspended in 10 mM TRIS-150 mM NaCl pH 7.5 buffer (approximately 0.94 mg/ml protein). The virions were solubilized 0.75% (v/v) Triton X100 and then ultracentrifuged at 150,000×g for 60 minutes to pellet the DNA core using a modification of the method described by Wells. (Wells A, Koide N, Klein G: Two large virion envelope glycoproteins mediate EBV binding to receptor-positive cells. J Virology 1982; 41:286–297.) Following dialysis, the supernatant EBV extract is characterized by both SDS-PAGE (denatured) and size exclusion HPLC (non-denatured).

Control (non-EBV) proteins are extracted from aliquots of Lambda phage virus using the same methods as described above.

Aliquots of the brushite particles weighing approximately 1.5 mg were initially suspended in 3.0 ml of 29.2 mM cellobiose solution in a dust free glass vial by liberal vortexing. The resultant suspension is then sonified at 175 W for 10.0 minutes at a frequency of approximately 20 kHz at 25° C. The dispersion is clarified by microcentrifugation at 16,000×g for 15 seconds. The remaining pellet is then discarded in favor of the supernatant. Unadsorbed cellobiose was removed by ultrafiltration against 20 mls of 25 mM phosphate reaction buffer (pH 7.40 25 mM $HPO_4^{2-}$/$H_2PO_4^{1-}$) in a 10 kD nominal molecular weight filtered stir cell under a 7.5 psi $N_2$ gas head at 37.5° C. Aliquots of the intermediate product are characterized by photon correlation spectroscopy and, following dialysis as described below, by doppler electrophoretic light scatter analysis.

The process of viral protein adsorption is initiated by the removal of the mild triton surfactant from 250 μl aliquots of EBV extract by ultrafiltration against 25 mls of phosphate reaction buffer at 4° C. in a 10 kD nominal molecular weight stir cell and then adjusted to a concentration of 1.0 μg/μl or approximately 1.0 ml final volume. Then 500 ul of the triton free EBV extract is quickly added to a MD nominal molecular weight stir cell with 2.0 ml of the surface treated tin oxide dispersion prewarmed to 37.5° C. The mixture is then slowly stirred while being incubated at 37.5° C. for 2.0 hours. After incubation the unabsorbed EBV extract is removed by ultrafiltration against 25 mls of phosphate reaction buffer.

Control (non-EBV) decoys fabricated with lambda phage viral protein extracts are synthesized using the same process described above.

Intermediate components, the final assembled decoys, and whole Epstein-Barr virions are characterized by doppler electrophoretic light scatter analysis to determine their electrophoretic mobility (surface charge) in a fluid phase. Nine phosphate buffer solutions having at 25° C. pH's ranging between 4.59 and 9.06 and corresponding conductivities ranging between 2.290 and 4.720 mS/cm are prepared. Aliquots of raw TCP, surface modified cellobiose covered TCP, synthesized EBV decoy, and whole EBV are dialyzed against each of the nine solutions and the mobilities of the particulates in dispersion are then measured at field strengths of 4.0, 5.5, 5.5, and 8.0 mA respectively. The mobility values acquired simultaneously by the 4 angled detectors of the instrument are averaged and the means of 3 measurements per dispersion are recorded.

The synthesized EBV decoys and control decoys are characterized by immunoagglutination photon correlation spectroscopy to determine the antibody reactivity of their surfaces. Positive reactivity is assessed by incubating the EBV decoy for 60 minutes at 37.5° C. with a cocktail of anti-EBV murine monoclonal antibodies (1ug each of anti-EBV-VCA, anti-EBV EA-R, anti-EBV MA, and anti EBV EA-D) in 15% lactose, 0.9% NaCl, 10 mM HEPES buffer, and 0.2% NaN3. Background reactivity is assessed by incubating the EBV decoy with irrelevant murine $IgG_1$. Specificity is assessed by reacting the lambda phage decoy with monoclonal anti-EBV murine antibodies. Agglutination is measured by photon correlation spectroscopy at a 90° angle.

Antibody affinity intensity is assessed by immunogold transmission electron microscopy using the particulates and antibodies listed above and then adding secondary anti-murine 30 nm gold-labeled antibodies (Faulk W, Taylor G. Immunocolloid method for electron microscopy, *Immunochemistry* 8:1081–1083, 1971).

Labeling of the EBV decoy (positive reaction) is accomplished by incubating a 20 μl mixture of murine monoclonals (1 μg anti-EBV-VCA and 1 μg anti-EBV EA-R in 15% lactose, 0.9% NaCl, 10 mM HEPES buffer, and 0.2% NaN3) with a fresh 0.5 ml sample of EBV decoy at 37.5° C. for 30 minutes in a 300 kD nominal molecular weigh stir cell. Unbound antibody is then removed by ultrafiltration against 20 mls of phosphate reaction buffer under a 5.0 psi $N_2$ pressure head. After washing, 50 μl of goat anti-murine antibody covalently fused to 30 nm gold spheres ($10^6$ particles/ml) is incubated with 200 μls of the labeled particles in a 1M nominal molecular weight stir cell at 37.5° C. for 30 minutes. Unbound secondary antibody is removed by ultrafiltration against 10 mls of phosphate reaction buffer.

Labeling of the EBV decoy (negative reaction) is accomplished by incubating 2.5 μl of murine polyclonal nonspecific IgG1 (1-μg/μl in 15 mM NaCl pH 7.4) with a fresh 0.5 ml sample of EBV decoy as described above followed by the same washing and gold-labeling steps. Labeling of the lambda phage control decoy (negative reaction) is accomplished by incubating a 20 μl mixture of murine monoclonal anti-EBV antibodies with the lambda phage virus coated decoy using the same procedure detailed above.

Immunolabeled particles are prepared for electron microscopy in two ways. A direct immersion technique where a carbon coated copper viewing grid is submersed into sample for approximately 5 seconds and then fixed in 5% glutaraldehyde for 1 minute, is used for all reactions as a fast screening technique. A more involved method adding glutaraldehyde directly to the reaction solution, then pelleting the product at 16,000×g for 5 minutes into 0.5 ml soft agar preparation (0.7% agarose in $H_2O$). Then the resultant agar plugs are embedded in plastic and sectioned into 0.1 μm sheets for viewing.

Analysis of both the positive and negative controls is performed by examining pelleted samples of the labeled reaction products by transmission electron microscopy. The relative intensity of antibody binding is determined by counting the number of tin oxide based particles observed to have bound gold spheres (% positive) and then noting the number of gold spheres bound to a given particle (intensity, number/event).

The ultrafine brushite particles will measure about 2 to 30 nm in diameter and will form aggregates measuring 50 to 200 nm in diameter by transmission electron microscopy. By photon correlation spectroscopy, these same particles when dispersed in distilled water produce agglomerates measuring about 150 nm. The brushite particles are fully crystalline as characterized by electron and x-ray diffraction. Energy dispersive x-ray spectroscopy should show no other elements present as impurities.

Characterization of the EBV proteins by SDS-PAGE should show two distinct protein bands. The first, existing as a dimer suggesting variable glycosylation, will exhibit a molecular weight of approximately 350 kd which is consistent with the predominant envelope glyco-protein of EBV. The second will exhibit a molecular weight of approximately 67 kd consistent with serum albumin which apparently adsorbs avidly to the viral surface. HPLC should confirm the presence of two distinct bands that exhibit spectrophotometric absorption maxima at 280 nm consistent with proteins. The predominant peak will have a chromatographic retention time of about 10.30 minutes and will be suppressed 90% by monoclonal anti VCA. The second and relatively minor peak will exhibit a chromatographic retention time of about 15.75 minutes similar to bovine serum albumin standards.

The previously described Doppler electrophoretic mobility studies conducted between the pH range of 4.5 to 9.0 will demonstrate 3 distinct patterns. First, both the decoy and native EB virus will retain virtually identical mobilities of approximately −1.4 μm-cm/V-s throughout the pH range. Second, untreated TCP will exhibit a mobility of approximately −1.0 μm-cm/V-s at a pH of 4.5 which then rose rapidly to −3.0 μm-cm/V-s at pH values of 5.0 and higher. Third, surface modified TCP treated with cellobiose should retain a mobility of approximately −1.5 μm-cm/V-s until it increased rapidly to −2.5 μm-cm/V-s at a pH of 7.5.

The previously described photon correlation spectroscopy will show that native EBV measured approximately 102+/−32 nm and the synthesized EBV decoy measured approximately 154+/−52 nm. Synthesized EBV decoy, when reacted with the monoclonal anti-EBV cocktail, should agglutinate to form 1534+/−394 nm masses. Synthesized EBV decoy, when reacted with non-specific mouse IgG, will only increase slightly in size with agglutination diameters of 230+/−76 nm. Lambda phage decoy, when reacted with the monoclonal anti-EBV cocktail, only increases slightly in size with agglutination diameters of 170+/−35 nm.

The previously described transmission electron microscopy of anti-EBV antibody labeled EBV decoy particles will reveal a positive gold staining frequency of about 23.51%+/−5.53 with an average staining intensity of 7.41 gold labels per event. Examination of nonspecific mouse IgG antibody labeled EBV decoy particles will reveal a positive gold staining frequency of 5.53%+/−2.04 with an average staining intensity of 1.00 gold labels per event. Examination of anti-EBV antibody labeled lambda phage decoy particles will reveal a positive gold staining frequency of 7.21%+/−1.26 with an average staining intensity of 1.06 gold labels per event.

EXAMPLE 5

In Vivo Elicitation of Antibodies By Epstein-Barr Virus Decoy

Four sensitization solutions are prepared and delivered once every other week by intramuscular injection in three 250 μl aliquots to New Zealand rabbits aged approximately 8 weeks. The first four animals receive approximately $10^9$ whole EBV virions (approximately 32 μg of gp350 estimated by integration of the spectrophotometric absorption curve at 280 nm against a 25 μg bovine serum albumin standard) dispersed in phosphate reaction buffer per injection. The second four animals receive 32 μg per injection of isolated and purified gp350 using the same injection protocol. The third group receives EBV viral decoys (Example 4) synthesized from a starting aliquot of 32 μg of gp350 per injection. The last group receives cellobiose coated TCP particles dispersed in phosphate reaction buffer. Injections are free of adjuvant. Whole blood is removed using aseptic techniques via cardiac puncture 2 weeks following each of the three injections and the animals are terminated by cardiac puncture followed by lethal sedation at 6 weeks. Serum is extracted by microcentrifugation at 16 kg of whole blood for 1 minute and then stored frozen at −70° C. pending analysis.

Immunospecific antibody against whole EBV virions (ABI) is assayed by ELISA. Approximately $10^9$ virions/ml in phosphate reaction buffer are diluted 1:10 in coating buffer and then allowed to adsorb overnight at 4° C. in polycarbonate assay plates (Falcon). Rabbit serum affinity for the bound EBV virions is determined by the colorimetric reaction of goat anti-rabbit IgG alkaline phosphatase (Sigma) developed with para-nitrophenyl phosphate. The concentration of immunospecific IgG is determined by comparison to a calibration curve using nonspecific rabbit IgG as the adsorbed antigen and by subtracting the baseline values recorded from the wells containing serum from the rabbits stimulated with TCP only.

Serum collected from the 4 rabbits sensitized with TCP particles will show no increased anti-EBV activity over pre-immune serum at any of the three two week sampling intervals. The remaining 3 groups will show a progressive rise in the concentration of anti-EBV specific IgG over the 6 week period. Animals sensitized with purified EBV proteins alone will show a maximum of approximately 0.05 ug/μl anti-EBV IgG at six weeks. In contrast, animals sensitized with either whole EBV or decoy EBV will exhibit a statistically significant four fold greater response with approximately 0.20 μg/ul of anti-EBV IgG at six weeks. The immunospecific responses to decoy EBV and whole EBV will be virtually identical.

As is apparent from Examples 4 and 5, the synthesized EBV decoy in accordance with the present invention possesses the same surface charge as native virus, is recognized specifically and avidly by monoclonal antibodies, and evokes immunospecific antibodies with the same effectiveness as whole virus. Using photon correlation spectroscopy, the number of particles that agglutinated in the three reaction conditions can be calculated from the measured diameters of the aggregates. These calculations will indicate that monoclonal anti-EBV antibodies produce agglutinated masses consisting of an average of about 1000 decoy EBV particles. Non-specific mouse IgG antibodies produce agglutinated masses consisting of an average of less than 5 decoy EBV particles, while monoclonal anti-EBV antibodies produce agglutinated masses consisting of an average of about 1 to 2 decoy control lambda phage particles. These expected results show that the agglutination potential of the EBV decoy in accordance with the present invention is almost three orders of magnitude greater than controls. The immunogold transmission electron microscopy will show that the gold labeled antibody staining of anti-EBV labeled EBV decoys is 25 to 30 times greater than controls. The ELISA analysis of the immunospecificity of anti-EBV IgG elicited in the rabbits by the EBV decoy is similar to the response elicited by native virus and is expected to be 4 fold greater than the response elicited by isolated purified proteins.

EXAMPLE 6

Preparation of HIV Decoys

The following procedure is used to adsorb HIV membrane antigens onto TCP (Brushite) nanocrystalline particles to provide HIV decoys.

HIV Workup 1.0 ml of HIV (TCID 50 titre which varied between $10^{5.75}$ to $10^{7.17}$ as determined by the producer Advanced Biotechnology, Inc.) is dialyzed into PBS by 100 KD ultrafiltration and frozen down to $-70°$ C. until needed. On injection day the vital stock is thawed on ice and diluted to 1:25 in PBS. 100 ul of this preparation is used for injection. 1.0 ml of HIV ($10^{5.75}$ transforming units per ml) is added to 0.5 ml of envelope extraction buffer and is allowed to incubate for 1.0 hr at room temp. The extract is then ultracentrifuged at 100 K*g for 2.0 hrs at $4.0°$ C. to remove nucleocapsid. Removal of Triton X and envelope protein enrichment is accomplished by incubation with a 300 μl slurry of polystyrene micro beads and subsequent 100 kD ultra filtration into PBS. For a 100 ul injection the extract volume is corrected to a 1.0 ml volume and diluted 1:25 in PBS or to a protein concentration of around 2.5 ug/100 ul/injection volume. Protein quantization is conducted by HPLC. HPLC conditions are as follows: Waters GFC SW300/Mobile phase: 300 mM NaCl, 20 mM phosphates pH 7.4/one major peak with a retention time of around 8.9 minutes at a flow rate of 0.5 ml per min/Integration is done against BSA standards.

Preparation of HIV Decoy

HIVex is adjusted to 1.0 ml volume after being ultrafiltered against pH 7.40 20 mM phosphate buffer and is incubated with 1.0 ml of diamond particles which has been coated with 500 mM cellobiose at $4.0°$ C. for 24 hours. The TCP particles will have an average particle size on the order of 50 nm. After adsorption, the decoy dispersion is prepared for injection by 300 kD ultrafiltration against PBS to remove unadsorbed protein and is adjusted to 1.0 ml with PBS and parceled out for ten 100 μl injections.

Immunological Activity of HIV Decoy

Rabbits, guinea pigs, and mice are injected with either live virus, protein extract, protein extract mixed with Freund's adjuvant, or the HIV decoy virus. Antibody titres against whole virus are measured by ELISA and characterized by western blotting. Cell mediated reactivity is assessed in the guinea pigs by dermal skin challenge with live virus follows by biopsy.

At physiological pH, the mean electrophoretic mobility and average dispersion diameter (50 nm) of these synthetic carriers closely mimicks that of their infectious counterparts. Vaccination of mouse, guinea pig, and rabbit with the HIV decoy will elicit the production of antisera which exhibits specific binding to whole HIV preparation as measured by ELISA. The histological analysis of earprick sites for animal sensitized to decoy virus and whole virus will show similar (qualitative and quantitative) reactions which differ significantly from both Freund's-sensitized animals and purified protein-sensitized animals at 1, 2, 7 and 24 weeks. Binding specificity can be confirmed by Western blots.

As shown in the above example, the HIV decoy of the present invention has a number of characteristics which are shared with native whole HIV virus. These characteristics include: size, surface charge, immunorecognition, ability to elicit comparable antibody titers, and the magnitude and character of cellular response. These attributes show that the decoy virus in accordance with the present invention can function effectively as a vaccinating agent.

Methods of obtaining meticulously clean biodegradable nanocrystalline particle; and methods for immobilizing (a) member(s) of a BRP are described in the additional examples below.

EXAMPLE 7

Preparing Meticulously Clean Biodegradable Nanoparticles

1. Prepare 6 clean sonication tubes with 500 mg of biodegradable particles per tube.

2. In fume hood, fill tubes with HCl (10N) approx. 8 ml/tube.

3. Sonicate for 30 min. (full power/$25°$ C.); three tubes per sonication treatment.

4. Centrifuge 30 min. at 2000 rpm.

5. Decant the acidic supernatant (in the fume hood), fill the tubes with HPLC grade water and then vortex.

6. Sonicate for 30 min and centrifuge for 30.

7. Decant the supernatant, and fill the tubes with HPLC grade water and vortex.

8. Repeat steps 7 and 8 two more times.

9. Decant the preparation into a clean glass baking dish.

10. Anneal at 210° C. overnight.

11. Remove the dried biodegradable crystals by gentle scraping with a clean unpainted spatula and transfer into 6 clean glass sonicating tubes.

12. Repeat steps 3 through 8.

13. Prepare a 10 kD (NMWL) 150 ml ultrafiltration cell, empty the contents only one of the tubes into the cell, and wash 500 ml of HPLC grade water through the cell under a $N_2$ pressure head of 20 psi (regulator pressure gauge reading).

14. After washing, adjust the preparation volume to 100.0 ml by using the appropriate volume markings on the side of the cell.

15. Take a concentration measurement by removing 1.0 ml of the preparation from the cell and lyophilizing it down in a pre-weighed 1.7 ml Eppendorf tube. After lyophilization, take a mass measurement of the tube with its contents and subtract it away from the mass of the empty tube. This provides the initial density of the preparation. Preferably, the concentration or density of the particles in the solution is about 10 mg/ml. If the initial density is lower than 10 mg/ml, then the solution should be further concentrated in the ultrafiltration cell.

EXAMPLE 8

Coating Meticulously Clean Biodegradable Nanoparticles with a Molecular Stabilizing Film (Cellobiose) Incubation/ Lyophilization 1. Sonicate the meticulously clean biodegradable particles (aqueous dispersion) prepared in Example 7 for 30 minutes at 25° C. at full power.

2. Then as quickly as possible, exchange suspending medium from water (stock) to a solution of 500 mM cellobiose using either a bench top microcentrifuge (30 seconds, full speed of 14,000 RPM) for small volumes or for larger volumes a floor models centrifuge (model 21K, in 50 ml centrifuge tubes, 8,000 RPM for a maximum of 2 minutes). Suspend the pelleted particles with 500 mM cellobiose, sonicate to aid dispersion (approximately 5 minutes at 25° C. at full power) and finally set the mixture on a rocking plate overnight in a cold room.

3. The next day portion out the mixture into appropriately sized vessels for overnight lyophilization.

4. Leave the tubes capped with a layer of parafilm around the cap and place them in a freezer until the washing step.

5. Reconstitute the particle/cellobiose in a suitable buffer depending on the application. Suitable buffers are low ionic strength buffered phosphate (PRB), water, or bicarbonate. Reconstitution in the buffer is accomplished by vortexing and a 5 minute sonication.

6. Wash by repeated centrifugation (using either a bench top microcentrifuge for small volumes or for large volumes a floor model centrifuge) and resuspension into the buffer.

7. Take a concentration measurement by removing 1 ml of the suspension dehydrating it in a lyophilizer in a pre-weighed 1.7 ml Eppendorf tube, and massing.

8. Calculate the final volume necessary to bring the concentration to 1 mg/ml. Add enough buffer to bring the concentration of the particle/cellobiose preparation to 1 mg/ml.

EXAMPLE 9

Immobilizing a Member of Biochemically Reactive Pair (BRP) to a Coated Meticulously Clean Solid Surface 1. Murine Lymphotropic virus (MuLV) extraction: MuLV stock diluted 1:5 (e.g. 1 ml stock virus diluted to a final volume of 5 ml with the dilutant) with Triton X-100 extraction buffer and is allowed to incubate overnight at 4° C. The extract is then ultracentrifuged at 100 K*g for 2.0 hours at 4° C. to remove the nucleocapsid.

2. Pellet is discarded in favor of supernatant.

3. MuLV decoy synthesis: It is desirable to use aseptic technique throughout the synthesis. Setup the stir cell unit such that access to the reaction mixture is rigorously controlled. Transfer the MuLV extract to a 100 kd filter unit of 10 ml volume and add the particle/cellobiose cores to a final concentration of 1 mg/ml. Begin continuous dialysis using a total of 200 ml fresh, sterile PRB (20 mM phosphate, pH 7.4). If the decoy is being prepared for injection, adjust to a final volume of 1.0 ml and dilute to 1:25 with PBS for a 100 ul injection. For all other uses, the decoy is stored at 4° C. in PRB.

EXAMPLE 10

Preparing Meticulously Clean Particles of Brushite

Reagents 0.75M $CaCl_2$: 55.13 g $CaCl_2.2H_2O$ is dissolved with HPLC grade water to 0.500 L in a volumetric flask. Filter sterilize with 0.2 um sterile filtration unit and place in a sterile 500 ml culture medium flask. Store at room temperature.

0.25M $Na_2HPO_4$: 17.75 g of anhydrous $Na_2HPO_4$ is dissolved with HPLC grade water to 0.500 L in a volumetric flask. Filter sterilize with 0.2 um sterile filtration unit and place in a sterile 500 ml culture medium flask. Also store at room temperature.

Brushite Synthesis

About a half hour before synthesis, prepare the sonicator by cooling down the cup horn. This is accomplished by adjusting the low temperature thermostat on the water condenser to 4° C. and dialing a setting of "4" on the peristatic circulator. Once the 4° C. mark is reached, prepare 50.0 ml of 0.75M $CaCl_2$ and 50.0 ml of 0.25M $Na_2H_2PO_4$ and load into 50 ml syringes. The syringes are then to be connected to a 3-way luer lock connector so that they are set in diametric opposition—allowing the remaining luer port to be free to dispel product. Once the mixing apparatus is set up, place a sterile 120 ml sonicating flask in the cup horn and slowly power up the sonicator to 100% power. Position the mixing apparatus so that the free luer port is over the sonicating flask. Expel syringe contents into the flask as rapidly and evenly as possible so as to empty each syringe roughly at the same time. Then quickly secure a polypropylene liner over the sonicating flask and let sonicate for an additional 15 minutes.

Brushite Washing

Roughly divide the preparation into two 50 ml blue top polypropylene tubes and pellet at 2000 rpm for 10 minutes (room temperature). Reconstitute by vortexing each pellet with sterile HPLC grade water to 50 ml (or tube capacity) and pellet at 2000 rpm for 10 minutes. Repeat this wash 3 more times and reconstitute the last pellets to 50.0 ml.

Transfer the dispersion to a sterile 120 ml sonicating flask with polypropylene liner. Place the flask in a previously cooled sonicator cup horn at 1° C. Sonicate at 100% power for 60 minutes.

EXAMPLE 11

Coating Meticulously Clean Particles of Brushite with a Molecular Stabilizing Film of Pyridoxyl-5-Pyrophosphate Brushite/Pyroxidal 5 phosphate (vitamine B6)

Pellet 100 ml of the dispersion prepared in Example 10 so that the entire contents can be transferred to a 50 ml conical tube. Adjust the tube volume to 40.0 ml. Then transfer the contents in 10 ml aliquots to four 15 ml conical tubes. Dissolve 1000 mg of Pyroxidal-5-phosphate with 800 μl of 10N NaOH and adjust with water to 10 mls. Filter sterilize this clear yellow solution with a 0.2 μm acrodisc and add 2.5 ml aliquots to each of the previously prepared 4 brushite tubes. Vortex each tube a few seconds to make certain that the contents are well dispersed. Lyophilize overnight at the low drying rate setting. The next morning resuspend in 50 ml aliquots of sterile HPLC grade water five more times. Pellet once more and transfer the pellets to four 15 ml conical tubes and adjust the final preparation volume with water to 40.0 ml.

EXAMPLE 12

Coating Meticulously Particles of Brushite With a Molecular Stabilizing Film of Citrate Brushite/citrate Pellet the 100 ml of the dispersion prepared in Example 13 so that entire contents can be transferred to a 50 ml conical tube. Adjust the tube volume to 40.0 ml. Then transfer the contents in 10 ml aliquots to four 15 ml conical tubes. Add 10 ml of 100 mM citrate to each of the 15 ml conicals and nutate for 30 minutes at room temperature. Lyophilize overnight at the low drying rate setting. The next morning resuspend in 50 ml aliquots of sterile HPLC grade water five more times. Pellet once more and transfer the pellets to four 15 ml conical tubes and adjust the final preparation volume with water to 40.0 ml.

EXAMPLE 13

Immobilizing Insulin on Brushite

Insulin Addition 100 units of insulin is added to each of the four 10 ml suspension prepared in Example 15 and then agitated on a nutator at 4° C.:

1) Lyophilization: Two of the core preparations are lyophilized overnight on a Savant Speed Vac (SVC100) under the low drying rate setting for approximately 16 hours. The next morning the lyophilate is resuspended to 10 ml with HPLC grade sterile water. Three washes with water are performed by pelleting and resuspension. Activity is determined during each wash by removing successive 1.0 ml aliquots and measuring the adsorption of light at 272 nm. Once it is determined that there is no activity in the supernatant (carrier) the preparation will have about 4.0 units per ml for injection. A typical injection is 500 ul.

If desired, the Brushite particles with the insulin immobilized thereon can be encapsulated in phospholipid the targeting layer as follows:

After insulin lyophilization, bring each of the preparations up to 10.0 ml with a water dispersion of 10% phosphatidyl choline, 10% phosphatidyl serine, and 5% water soluble cholesterol (Sigma Biochemical). Allow the mixture to incubate overnight at 4° C. on a rocker. The next morning extrude the mixture through a 19 gauge needed without promoting significant foaming. Then three washes with water are performed by pelleting and resuspension. Activity is determined during each wash by removing successive 1.0 ml aliquots and measuring the adsorption of light at 272 nm. Once it is determined that there is no activity in the supernatant (carrier) the preparation will have about 4 units per ml for injection. A typical injection is about 500 ul.

EXAMPLE 14

Preparation of Cellobiose Coated Brushite Particle with Hemoglobin Bound Thereto The following example demonstrates the preparation of Brushite particle having hemoglobin bound thereto in accordance with the present invention. The fabrication process involved coating ultrafine nanocrystalline Brushite particles with a glassy film of disaccharides and then physically adsorbing purified hemoglobin. The assembly was then coated with phospholipid.

One (1.00) g. of ultrafine particles prepared as in Example 7 was dispersed in 5.0 ml of 100 mM cellobiose (Sigma) solution with 175 watt sonication (Branson) for 10 minutes. The colloid was then incubated at 4.0° C. overnight in a 10 kD stir cell. The following day, this colloid was lyophilized for 24 hours and reconstituted in 1.0 ml of ddH$_2$O. Unabsorbed cellobiose was removed by 10 kD stir cell ultra filtration (UF) (Filtron) against 100 ml of 20 mM phosphate buffer (pH 7.4) (PRB) and corrected to 2.0 ml. (UF) (Filtron) against 100 ml of 20 mM phosphate buffer (pH 7.4) (PRB) and corrected to 2.0 ml.

Five hundred (500) mg of human hemoglobin type A$_o$ (Sigma) was dissolved in 5.0 ml PBS (pH 6.8) (Gibco) and then ultrafiltered against 150 ml PRB at 4.0° C. in a 50 kD stir with 30 psi N2. The filtrate was adjusted to 3.0 ml. The surface modified Brushite dispersion (2.0 mL) was then added to the 50 kD ultrafiltrate cell and allowed to incubate overnight with slow stirring (5 psi N$_2$). The filtrate was adjusted to 3.0 ml. The surface modified diamond dispersion (2.0 mL) was then added to the 50 kD ultrafiltrate cell and allowed to incubate overnight with slow stirring (5 psi N2, 4.0° C.). The next morning, 35 uL of phosphatidyl dipalmitoyl serine (10 mM of 6.0 mM NaOH) (Sigma), 50 uL of phosphatidyl dipalmitoyl choline Sigma, and 8.7 uL of cholesterol (Sigma) was stirred in and incubated for approximately 6.0 hours. The final product was again filtered in a 50 kD ultrafiltration cell over 30 psi N$_2$ against 20 ml PBS (pH 7.4, 4.0° C. and adjusted to 5.0 ml for an estimated hemoglobin concentration of 10 g/dL.

EXAMPLE 15

Preparation of P5P Coated Brushite Particle with Hemoglobin Bound Thereto

In this example, red blood cell surrogates are made in the same manner as Example 14 except that pyridoxal-5-phosphate is substituted for cellobiose as the oxygen carrier anchor coating.

50 mg of acid cleaned particles was dispersed by 175 watt sonication (Branson) for 10 minutes, mixed with 75.0 mg of pyridoxal-5-phosphate and adjusted to 10.0 ml with deionized water. The mixture was spun lyophilized overnight, washed with 4–10 ml aliquots of deionized water and reconstituted to 25 mg/ml in pH 7.40, 20 mM phosphate buffer.

4.0 ml of nanocrystalline core particles were added to 1.0 ml recovered red blood lysate hemoglobin. The mixture was then slowly dialyzed into 100 ml of 0.5× PRB overnight at 4.0° C. under a nitrogen head of 20 psi and through a 10 kD ultrafiltration cell. The next morning, 34 uL of phosphatidyl serine (Sigma), 50 uL of cholesterol (Sigma) was stirred in and incubated for approximately 6.0 hours. The final product was again filtered to remove free hemoglobin in a 50 kD ultrafiltration cell over 30 psi $N_2$ against 200 ml PBS (pH 7.4, 4.0° C.) and adjusted to 1.0–2.5 ml or an estimated hemoglobin concentration of 10 g/dL.

The preceding procedure was repeated at different pyridoxal-5-phosphate concentrations. As a result, red blood cell surrogates were prepared wherein the nanocrystalline particles were coated in solutions containing 1 mM pyridoxal-5-phosphate and 30 mM pyridoxal-5-phosphate.

The red blood cell surrogates prepared in Examples 14 and 15 were analyzed for oxygen dissociation characteristics as well as size distribution, electrophoretic mobility and retained molecular conformation. The red blood cell surrogates coated with cellobiose (Example 14) exhibited an oxygen dissociation (P50) of about 26–30 30 mm Hg. The red blood cell surrogates having coatings of pyroxidal-5-phosphate should have oxygen dissociations (P50) of about 37 mm Hg. This compares well with the oxygen dissociation of whole human blood which is 31 mm Hg. In addition, hemoglobin-bound nanocrystalline particles were prepared in the same manner as Example 14 except that the coating of lipid was deleted. The oxygen-dissociation of the lipid-free hemoglobin-bound nanocrystalline particles was about 10 mm Hg.

The electrophoretic mobility of the red blood cell surrogates produced in Examples 14 and 15 were measured with Doppler electrophoretic light scatter analysis (DELSA 440, Coulter Electronics, Inc., Hialeah, Fla.). The electrophoretic mobility was −1.7 um cm/Vs at a pH of 7.4 PRGB BUFFER at 25° C.

The size distribution of the red blood cell surrogates produced in Examples 14 and 15 were measured by both photon correlation spectroscopy at a 90° angle in PRB buffer at 22.5° C. (N4MD, Coulter) and by transmission microscopy (TEM, Zeiss 190). The red blood cell surrogates measured about 200 nanometers by photon correlation. For electron microscopy, a 10 microliter drop of particles in solution was placed on a paraffin surface which included a carbon-stabilized FORMVAR GRID (Ted Pella, Inc., Redding, Calif.) which was floated on top of the drop. Due to the high surface charge of the TEM GRID, the red blood cell surrogates absorbed to the grid allowing excess solution to be removed by careful blotting. A similar method was then used to stain the particles with 2% phosphotungstic acid. The stained grid was then dried and the red blood cell surrogates identified as having particle sizes in the range of 50–100 nanometers.

The conformational integrity of the red blood cell surrogates was verified by immunogold antibody affinity intensity. After being deposited on one nanometer TEM copper grids, the protein bound particles were incubated for one hour at 27° C. with polyclonal rabbit anti-human hemoglobin antibodies (Dako) and secondary goat anti-rabbit 30 nanometer gold-labeled antibodies (Zymed Laboratories, San Francisco, Calif.). The gold-labeled anti-bodies were observed to attach avidly to the hemoglobin present in the red blood cell surrogates.

EXAMPLE 16

Preparation of P5P Coated Brushite Particle with Taxol Bound Thereto

In this example, drug delivery vehicles are made in the same manner as Example 14 except that taxol is substituted for hemoglobin.

50 mg of cleaned particles was dispersed by 175 watt sonication (Branson) for 10 minutes, mixed with 75.0 mg of pyridoxal-5-phosphate and adjusted to 10.0 ml with deionized water. The mixture was spun lyophilized overnight, washed with 4–10 ml aliquots of deionized water and reconstituted to 25 mg/ml in pH 7.40, 20 mM phosphate buffer.

4.0 ml of nanocrystalline core particles were added to 1.0 ml solubilized taxol (100 mg/10 ml dd $H_2O$. The mixture was then slowly dialyzed into 100 ml of 0.5× PRB overnight at 4.0° C. under a nitrogen head of 20 psi and through a 10 kD ultrafiltration cell and then lyophilized. The next morning, 34 uL of phosphatidyl serine (Sigma), 50 uL of cholesterol (Sigma) was stirred in and incubated for approximately 6.0 hours. The final product was again filtered in a 50 kD ultrafiltration cell over 30 psi $N_2$ against 200 ml PBS (pH 7.4, 4.0° C.).

The entire contents of all references cited hereinabove are hereby incorporated by reference.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A biochemically active composition of matter comprising:

a biodegradable core particle comprising a polymer or ceramic having a diameter of less than about 1000 nanometers;

a coating comprising a substance that provides a threshold surface energy to said core particle which is sufficient to bind biochemically active agents without denaturing said agents, said substance covering at least a part of the surface of said core particle and said substance being a carbohydrate; and at least one biochemically active agent bound to said coated core particle wherein said biologically active agent bound to said core particle is not denatured to thereby provide said biochemically active composition.

2. A composition of matter according to claim 1 wherein said biochemically active agent is hemoglobin.

3. A composition of matter according to claim 1 wherein said core particle comprises a biodegradable ceramic selected from the group consisting of brushite and tricalcium phosphate.

4. A composition of matter according to claim 1 wherein said composition further comprises an outer coating of a phospholipid which comprises target ligands.

5. A composition of matter according to claim 1 wherein said biochemically active agent is one or both members of a bioreactive pair.

6. A composition of matter according to claim 1 wherein said coating comprises citrate, cellobiose or pyridoxal-5-phosphate.

7. A composition of matter according to claim 1 wherein said biologically active agent is a viral protein fragment.

8. A composition of matter according to claim 4 wherein said biologically active agent is a drug.

* * * * *